United States Patent [19]
Christensen et al.

[11] 4,208,330
[45] Jun. 17, 1980

[54] O-DERIVATIVES OF THIENAMYCIN

[75] Inventors: Burton G. Christensen, Metuchen; William J. Leanza, Berkeley Heights, both of N.J.

[73] Assignee: Merck & Co., Inc., Rahway, N.J.

[21] Appl. No.: 861,234

[22] Filed: Dec. 16, 1977

Related U.S. Application Data

[63] Continuation-in-part of Ser. No. 733,655, Oct. 18, 1976, abandoned, which is a continuation-in-part of Ser. No. 634,006, Nov. 21, 1975, abandoned.

[51] Int. Cl.$^2$ ............................................ C07D 487/04
[52] U.S. Cl. .......................... 260/326.31; 260/245.2; 260/326.25; 260/326.12 R; 424/250; 424/263; 424/267; 424/269; 424/270; 424/272; 424/273; 424/274; 542/416; 544/144; 544/282; 544/316; 544/335; 544/353; 544/373; 546/174; 546/200; 546/272; 548/336
[58] Field of Search .................... 260/326.31; 424/274

[56] References Cited

U.S. PATENT DOCUMENTS 3,950,357  4/1976  Kahan et al. .................... 260/326.31

Primary Examiner—Mary C. Lee
Attorney, Agent, or Firm—Hesna J. Pfeiffer; James A. Arno; Julian S. Levitt

[57] ABSTRACT

Disclosed are O- derivatives (esters and ethers of the secondary alcohol group) of the antibiotic thienamycin which has the following structure:

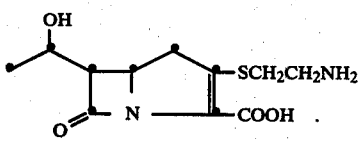

Such derivatives are useful as antibiotics. Also disclosed are processes for the preparation of such derivatives, pharmaceutical compositions comprising such derivatives, and methods of treatment comprising administering such derivatives and compositions when an antibiotic effect is indicated.

2 Claims, No Drawings

O-DERIVATIVES OF THIENAMYCIN

BACKGROUND OF THE INVENTION

This application is a continuation-in-part of co-pending U.S. patent application Ser. No. 733,655, filed Oct. 18, 1976 which, in turn, is a continuation-in-part of co-pending U.S. patent application Ser. No. 634,006, filed Nov. 21, 1975, both now abandoned.

This invention relates to certain O-derivatives of the new antibiotic thienamycin. By "O-derivatives" is meant derivatives such as esters and ethers of the secondary alcoholic function of thienamycin. Such derivatives are useful as antibiotics.

This invention also relates to processes for the preparation of such compounds, pharmaceutical compositions comprising such compounds, and methods of treatment comprising administering such compounds and compositions when an antibiotic effect is indicated.

Thienamycin may serve as the starting material for the preparation of the compounds of the present invention. It is disclosed and claimed in co-pending, commonly assigned U.S. patent application Ser. No. 526,992, filed Nov. 25, 1974, (now U.S. Pat. No. 3,950,357, issued Apr. 13, 1976); said application is incorporated herein by reference for the disclosure relative to the preparation and isolation of thienamycin. Thienamycin is known to have the following structural formula:

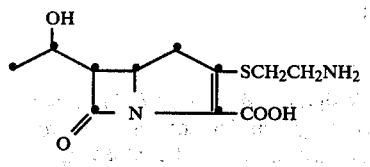

Thienamycin and all of its isomers (in pure form and as mixtures) are also obtainable by the total synthesis disclosed and claimed in co-pending, commonly assigned U.S. patent application Ser. No. 833,210 (Sept. 15, 1977), now abandoned. This application is incorporated herein by reference to the extent that it makes available all isomers of I as starting materials in the preparation of the compounds of the present invention.

The O-derivatives of thienamycin of the present invention may be depicted by the following generic structural formula (II):

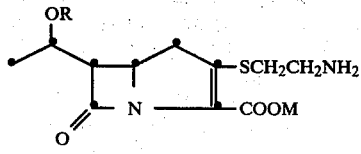

or more conveniently by the symbol (II):

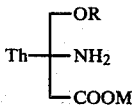

wherein "Th" symbolizes the bicyclic nucleus of thienamycin and the OH, amino and carboxyl groups of thienamycin are illustrated; M is hydrogen, a salt cation selected from the alkali or alkaline earth metals or an amine salt; and R is (1) acyl (generically the group OR is classifiable as an ester); or (2) R is selected from alkyl, aryl, aralkyl and the like (such that the group OR is generically classifiable as an ether). The term "acyl" is by definition inclusive of the alkanoyls including derivatives and analogues thereof such as thio analogues wherein the carbonyl oxygen is replaced by sulphur; as well as sulphur and phosphorous acyl analogues such as substituted sulfonyl-, sulfinyl- and sulfenyl-radicals, and substituted P(III and V) radicals such as substituted phosphorous-, phosphoric-, phosphonous- and phosphonic-radicals, respectively. Such acyl radicals of the present invention are further defined below, as are the radicals ((2), above) which constitute the ether embodiments of the present invention.

There is a continuing need for new antibiotics. For unfortunately there is no static effectiveness of a given antibiotic because continued wide scale usage of any such antibiotic selectively gives rise to resistant strains of pathogens. In addition, the known antibiotics suffer from the disadvantage of being effective only against certain types of microorganisms. Accordingly the search for new antibiotics continues.

Unexpectedly, it has been found that the compounds of the present invention are broad spectrum antibiotics, which are useful in animal and human therapy and in inanimate systems.

Thus it is an object of the present invention to provide a novel class of antibiotics which possess the basic nuclear structure of the antibiotic thienamycin but which are characterized as O-derivatives thereof. These antibiotics are active against a broad range of pathogens which representatively include both gram positive bacteria such as *S. aureus, S. pyogenes,* and *B. subtilis* and gram negative bacteria such as *E. coli, Proteus morganii,* and *Klebsiella.* Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

In the generic representation of the compounds of the present invention (II, above) the acyl radical represented by R can, inter alia, be substituted or unsubstituted aliphatic, aromatic or heterocyclic, aralphatic or heterocyclylaliphatic carboxylic acid radical, a substituted or unsubstituted carbamyl radical or a carbothioic acid radical. One group of acyl radicals can be represented by the general formula:

wherein X is O or S and R" represents hydrogen; amino; substituted amino such as alkyl- and dialkylamino wherein the alkyl radical comprises 1 to about 6 carbon atoms; substituted or unsubstituted: straight or branched chain alkyl wherein the alkyl radical comprises 1 to about 6 carbon atoms; mercapto such as alkylthio, typically comprising 1 to 6 carbon atoms; arylthio, typically comprising 6 to 10 carbon atoms; hydroxy such as alkoxy, typically comprising 1 to 6 carbon atoms; aryloxy, typically comprising 6 to 10 carbon atoms; alkenyl, or alkynyl groups typically comprising 2 to 6 carbon atoms; aryl such as phenyl; aralkyl such as benzyl; cycloalkyl, typicall comprising 3 to 6 carbon atoms; or a heteroaryl or heteroaralkyl group (mono- and bicyclic) wherein the alkyl moiety typically comprises 1 to 3 carbon atoms and the heterocyclic ring comprises typically 4 to 10 atoms and the hetero atom or atoms are selected from O, N and S; such above-listed groups can be unsubstituted or can be substituted by radicals such as OH, SH, SR (R is loweralky or aryl such as phenyl), alkyl or alkoxy groups having 1 to about 6 carbon atoms, halo, such as Cl, Br, F and I, cyano, carboxy, sulfamino, carbamoyl, sulfonyl, azido, amino, substituted amino such as alkylamino including quaternary ammonium wherein the alkyl group comprises 1 to 6 carbon atoms, haloalkyl such as trifluoromethyl, carboxyalkyl, carbamoylalkyl, N-substituted carbamoylalkyl, wherein the alkyl moiety of the foregoing four radicals comprises 1 to about 6 carbon atoms, amidino, guanidino, N-substituted guanidino, guanidino lower alkyl and the like. Representative examples of such acyl groups that might be mentioned are those wherein R" is benzyl, p-hydroxybenzyl, 4-amino-4-carboxybutyl, methyl, cyanomethyl, 2-pentenyl, β,β-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)5-methyl-4-isoxazolyl, D-4-amino-4-carboxybutyl, D-4-N-benzoylamino-4-carboxy-n-butyl, p-aminobenzyl, o-aminobenzyl, m-aminobenzyl, p-dimethylaminobenzyl, (3-pyridyl)methyl, 2-ethoxy-1-napthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-guanidinophenyl)-4-isoxazolyl, 4-guanidinomethylphenyl, 4-guanidinomethylbenzyl, 4-guanidinobenzyl, 4-guanidinophenyl, 2,6-dimethoxy-4-guanidino, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, guanylthiomethyl, 4-pyridylmethyl, 5-iosxazolylmethyl, 4-methoxy-5-isoxazolylmethyl, 4-methyl-5-isoxazolylmethyl, 1-imidazolylmethyl, 2-benzofuranylmethyl, 2-indolylmethyl, 2-phenylvinyl, 2-phenylethynyl, 1-aminocyclohexyl, 2- and 3-thienylaminomethyl, 2-(5-nitrofuranyl)vinyl, phenyl, o-methoxyphenyl, o-chlorophenyl, o-phenylphenyl, p-aminomethylbenzyl, 1-(5-cyanotrizolyl)methyl, difluoromethyl, dichloromethyl, dibromomethyl, 1-(3-methylimidazolyl)methyl, 2- or 3-(5-carboxymethylthienyl)methyl, 2- or 3-(4-carbamoylthienyl)methyl, 2- or 3-(5-methylthienyl)methyl, 2- or 3-(methoxythienyl)-methyl, 2- or 3-(4-chlorothienyl)-methyl, 2- or 3-(5-sulfothienyl)methyl, 2- or 3-(5-carboxythienyl)methyl, 3-(1,2,5-thiadiazolyl)methyl, 3-(4-methoxy-1,2,5-thiadiazolyl)methyl, 2-furylmethyl, 2-(5-nitrofuryl)methyl, 3-furylmethyl, 2-theinylmethyl, 3-thienylmethyl, tetrazolylmethyl benzamidinomethyl and cyclohexylamidinomethyl The acyl group can also be a radical of the formula:

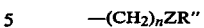

wherein X is O or S and n is 0–4, Z represents oxygen, sulfur, carbonyl or nitrogen and R" is defined as above. Representative members of the substituent —(CH$_2$)$_n$ZR"

that might be mentioned are allylthiomethyl, phenylthiomethyl, butylmercaptomethyl, α-chlorocrotylmercaptomethyl, phenoxymethyl, phenoxyethyl, phenoxybutyl, phenoxybenzyl, diphenoxymethyl, dimethylmethoxymethyl, dimethylbutoxymethyl, dimethylphenoxymethyl, 4-guanidinophenoxymethyl, 4-pyridylthiomethyl, p-(carboxymethyl)phenoxymethyl, p-(carboxymethyl)phenylthiomethyl, 2-thiazolylthiomethyl, p-(sulfo)phenoxymethyl, p-(carboxymethyl)phenylthiomethyl, 2-pyrimidinylthiomethyl, phenethylthiomethyl, 1-(5,6,7,8-tetrahydronaphthyl)oxomethyl, N-methyl-4-pyridylthio, benzyloxy, methoxy, ethoxy, phenoxy, phenylthio, amino, methylamino, dimethylamino, pyridinium methyl, trimethylammoniummethyl, cyanomethylthiomethyl, trifluoromethylthiomethyl, 4-pyridylethyl, 4-pyridylpropyl, 4-pyridylbutyl, 3-imidazolylethyl, 3-imidazolylpropyl, 3-imidazolylbutyl, 1-pyrroloethyl, 1-pyrrolopropyl and 1-pyrrolobutyl.

Alternatively, the acyl group can be a radical of the formula:

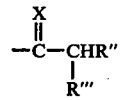

wherein R" is defined as above and R'" is a radical such as amino, hydroxy, azido, carbamoyl, guanidino, amidino, acyloxy, halo, such as Cl, F, Br, I, sulfamino, tetrazolyl, sulfo, carboxy, carbalkoxy, phosphono and the like. Representative members of the substituent

that might be mentioned are α-aminobenzyl, α-amino-(2-thienyl)methyl, α-(methylamino)benzyl, α-aminomethylmercaptopropyl, α-amino-3- or 4-chlorobenzyl, α-amino-3- or 4-hydroxybenzyl, α-amino-2,4-dichlorobenzyl, α-amino-3,4-dichlorobenzyl, D(—)-α-hydroxybenzyl, α-carboxybenzyl, α-amino-(3-thienyl)methyl D-(—)-α-amino-3-chloro-4-hydroxybenzyl, α-amino(-cyclohexyl)methyl, α-(5-tetrazolyl)-benzyl, 2-thienylcarboxymethyl, 3-thienyl-carboxymethyl, 2-furylcarboxymethyl, 3-furyl-carboxymethyl, α-sulfaminobenzyl, 3-thienyl-sulfaminomethyl, α-(N-methylsulfamino)-benzyl, D(—)-2-thienyl-guanidinomethyl, D(—)-α-guanidinobenzyl, α-guanylureidobenzyl, α-hydroxybenzyl, α-azidobenzyl, α-fluorobenzyl, 4-(5-methoxy-1,3-oxadiazolyl)-aminomethyl, 4-(5-methoxy-1,3-oxadiazolyl)-hydroxymethyl, 4-(5-methoxy-1,3-sulfadiazolyl)-hydroxymethyl, 4-(5-chlorothienyl-)aminomethyl, 2-(5-chlorothienyl)-hydroxymethyl, 2-(5-chlorothienyl)-carboxy-methyl, 3-(1,2-thiazolyl)-aminomethyl 3-(1,2-thiazolyl)-hydroxymethyl, 3-(1,2-thiazolyl)carboxymethyl, 2-(1,4-thiazolyl)-aminomethyl, 2-(1,4-thiazolyl)-hydroxymethyl, 2-(1,4-thiazolyl)-carboxymethyl, 2-benzothienylaminomethyl, 2-benzothienylhydroxymethyl, 2-benzothienylcarboxymethyl, α-sulfobenzyl, α-phosphonobenzyl, α-diethylphosphono and α-monoethylphosphono. Further acyl radicals of interest in this class when X=oxygen are:

wherein R³ and R⁴ are as defined below. R³ represents hydrogen, halo, such as chloro, fluoro, bromo, iodo, amino, guanidino, phosphono, hydroxy, tetrazolyl, carboxy, sulfo, or sulfamino and R⁴ represents phenyl, substituted phenyl, a mono- or bicyclic heterocyclyl containing one or more oxygen, sulfur or nitrogen atoms in the ring, such as furyl, quinoxalyl, thienyl, quinolyl, quinazolyl, thiazolyl, isothiazolyl, tetrazolyl, oxadiazolyl, thiadiazolyl and the like substituted heterocycles, phenylthio, phenyloxy, lower alkyl of 1-6 carbon atoms, heterocyclic or substituted heterocyclic thio groups; or cyano. The substituents on the moieties, R³ and R⁴, can be halo, carboxymethyl, guanidino, guanidinomethyl, carboxamidomethyl, aminoethyl, nitro, methoxy or methyl. When R³ is selected from the group consisting of hydrogen, hydroxy, amino or carboxy and R⁴ is selected from the group consisting of phenyl, or a 5- or 6-membered heterocyclic ring having one or two sulfur, oxygen or nitrogen hetero atom such as tetrazolyl, thienyl, furyl and phenyl, the following acyl radicals are representative: phenylacetyl, 3-bromophenylacetyl, p-aminomethylphenylacetyl, 4-carboxymethylphenylacetyl, 4-carboxyamidomethylphenylacetyl, 2-furylacetyl, 5-nitro-2-furylacetyl, 3-furylacetyl, 2-thienylacetyl, 5-chloro-2-thienylacetyl, 5-methoxy-2-thienylacetyl, α-guanidino-2-thienylacetyl, 3-thienylacetyl, 2-(4-methylthienyl)acetyl, 3-isothiazolylacetyl, 4-methoxy-3-isothiazolylacetyl, 4-isothiazolylacetyl, 3-methyl-4-isothiazolylacetyl, 5-isothiazolylacetyl, 3-chloro-5-isothiazolylacetyl, 3-methyl-1,2,5-oxadiazolylacetyl, 1,2,5-thiadiazolyl-4-acetyl, 3-methyl-1,2,5-thiadiazolylacetyl, 3-chloro-1,2,5-thiadiazolylacetyl, 3-methoxy-1,2,5-thiadiazolylacetyl, phenylthioacetyl, 4-pyridylthioacetyl, cyanoacetyl, 1-tetrazolylacetyl, α-fluorophenylacetyl, D-phenylglycyl, 4-hydroxy-D-phenylglycyl, 2-thienylglycyl, 3-thienylglycyl, phenylmalonyl, 3-chlorophenylmalonyl, 2-thienylmalonyl, 3-thienylmalonyl, α-phosphonophenylacetyl, α-amino cyclohexadienylacetyl, α-sulfaminophenylacetyl, α-hydroxyphenylacetyl, α-tetrazolylphenylacetyl and α-sulfophenylacetyl.

The acyl substituent may also be selected from sulphur (1) and phosphorous (2) radicals:

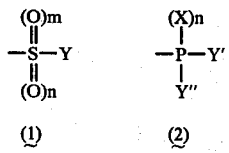

wherein with respect to (1), m and n are integers selected from 0 or 1 and Y=O⊖M⊕, —N(R″)₂, and R″; wherein M⊕ is selected from hydrogen alkali metal cations and organic bases; and R″ is as defined above, e.g., alkyl, alkenyl, aryl and heteroaryl. With respect to (2) X=O or S; n=0 or 1; and Y' and Y″ are selected from the group consisting of O⊖M⊕, —N(R″)₂, R″ and ZR″ wherein all symbolism is as defined above, e.g., R″ and ZR″ are representatively: alkyl, alkenyl, aryl, heteroaryloxy; Y' and Y″, including R″ moieties, can be joined together to form cyclic ester, ester-amide and amide functions. Illustrative examples of (1) are O-(methylsulphonyl)thienamycin, O-(o-nitrophenylsulphonyl)thienamycin, O-(p-chlorophenylsulphinyl)-thienamycin, O-(o-nitrophenylsulphenyl)thienamycin, O-sulphamoylthienamycin, O-dimethylsulphamoylthienamycin and thienamycin O-sulphonic acid sodium salt. Illustrative examples of (2) are O-(dimethoxyphosphino)thienamycin. O-(dibenzyloxyphosphino)thienamycin, O-(dihydroxyphosphino)thienamycin disodium salt, O-(dimethoxyphosphinyl)thienamycin, O-(dimethoxyphosphinothioyl)thienamycin, O-(dibenzyloxyphosphinyl)thienamycin, and O-(dihydroxyphosphinyl)thienamycin disodium salt.

An acyl class of particular interest is those acyl radicals, which are selected from the group consisting of conventionally known blocking or protective groups such as carbobenzyloxy, ring-substituted carbobenzyloxy such as o- and p-nitrocarbobenzyloxy, p-methoxycarbobenzyloxy, chloroacetyl, bromoacetyl, phenylacetyl, t-butoxycarbonyl, trifluoroacetyl, bromoethoxycarbonyl, 9-fluorenylmethoxycarbonyl, dichloroacetyl, o-nitrophenylsulfenyl, 2,2,2-trichloroethoxycarbonyl, bromo-t-butoxycarbonyl, phenoxyacetyl; non-acyl protective groups such as triloweralkyl silyl for example, trimethylsilyl and t-butyldimethylsilyl are also of interest.

The following radicals, according to the foregoing definition of acyl are preferred: formyl, propionyl, butyryl, chloroacetyl, methoxyacetyl, aminoacetyl, methoxycarbonyl, ethoxycarbonyl, methylcarbamoyl, ethylcarbamoyl, phenylthiocarbonyl, 3-aminopropionyl, 4-aminobutyryl, N-methylaminoacetyl, N,N-dimethylaminoacetyl, N,N,N-trimethylaminoacetyl, 3-(N,N-dimethyl)aminopropionyl, 3-(N,N,N-trimethyl)aminopropionyl, N,N,N-triethylaminoacetyl, pyridiniumacetyl, guanylthioacetyl, guanidinoacetyl, 3-guanidinopropionyl, N³-methylguanidinopropionyl, hydroxyacetyl, 3-hydroxypropionyl, acryloyl, propynoyl, malonyl, phenoxycarbonyl, amidinoacetyl, acetamidinoacetyl, amidinopropionyl, acetamidinopropionyl, guanylureidoacetyl, guanylcarbamoyl, carboxymethylaminoacetyl, sulfoacetylaminoacetyl, sulfo, phosphono, phosphonoacetylaminoacetyl, N³-dimethylaminoacetamidinopropionyl, ureidocarbonyl, dimethylaminoguanylthioacetyl, 3-(1-methyl-4-pyridinium)-propionyl, 3-(5-aminoimidazol-1-yl)propionyl, 3-methyl-1-imidazoliumacetyl, 3-sydnonylacetyl, o-aminomethylbenzoyl, o-aminobenzoyl,

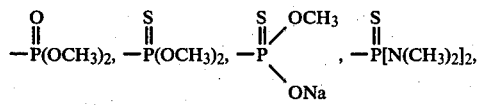

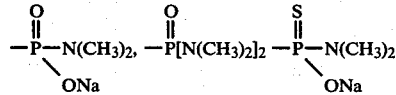

An especially preferred class of acyl radicals are terminally substituted acyls wherein the substituent is a basic group such as substituted and unsubstituted: amino, amidino, guanidino, guanyl, and nitrogen-containing mono- and bicyclic heterocycles (aromatic and non-aromatic) wherein the hetero atom or atoms, in addition to nitrogen, are selected from oxygen and sulphur. Such preferred substituted acyls may be represented by the following formula:

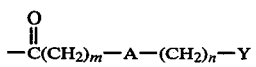

wherein m, and n are integers selected from 0 to 5; A is O, NR' (R' is hydrogen or loweralkyl having 1-6 carbon atoms), S or A represents a single bond; and Y is selected from the following group:

1. amino or substituted amino:

—N(R)₂ and —N⁺(R)₃ wherein the values for R are independently selected from: hydrogen; N(R')₂ (R' is hydrogen or loweralkyl having 1-6 carbon atoms); loweralkyl and loweralkoxyl having from 1 to 6 carbon atoms; loweralkoxyloweralkyl wherein the alkoxyl moiety comprises 1 to 6 carbon atoms and the alkyl moiety comprises 2-6 carbon atoms; cycloalkyl and cycloalkylalkyl wherein the cycloalkyl moiety comprises 3-6 carbon atoms and the alkyl moiety comprises 1-3 carbon atoms; two R groups may be joined together with the N atom to which they are attached to form a ring having 3-6 atoms.

2. amidino and substituted amidino:

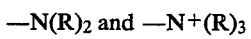

wherein the value of R is independently selected from the group consisting of: hydrogen; N(R')₂ (R' is hydrogen or loweralkyl having 1-6 carbon atoms); loweralkyl and loweralkoxyl having from 1 to 6 carbon atoms; loweralkoxyloweralkyl wherein the alkoxyl moiety comprises 1 to 6 carbon atoms and the alkyl moiety comprises 2 to 6 carbon atoms (when the loweralkoxyloweralkyl radical is attached to carbon the alkyl moiety comprises 1 to 6 carbon atoms); cycloalkyl and cycloalkylalkyl wherein the alkyl moiety comprises 1 to 3 carbon atoms; two R groups may be joined together with the atoms to which they are attached to form a ring having 3 to 6 atoms;

3. guanidino and substituted guanidino:

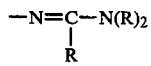

wherein R is as defined in 2. (above).

4. guanyl and substitued guanyl:

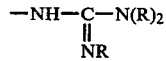

wherein R is as defined in 2. (above).

5. nitrogen-containing mono- and bicylic heterocycles (aromatic and non-aromatic) having 4 to 10 nuclear atoms wherein the hetero atom or atoms, in addition to nitrogen, are selected from oxygen and sulphur.

Such heterocycles are representatively illustrated by the following list of radicals (R' is H or loweralkyl having 1-6 carbon atom):

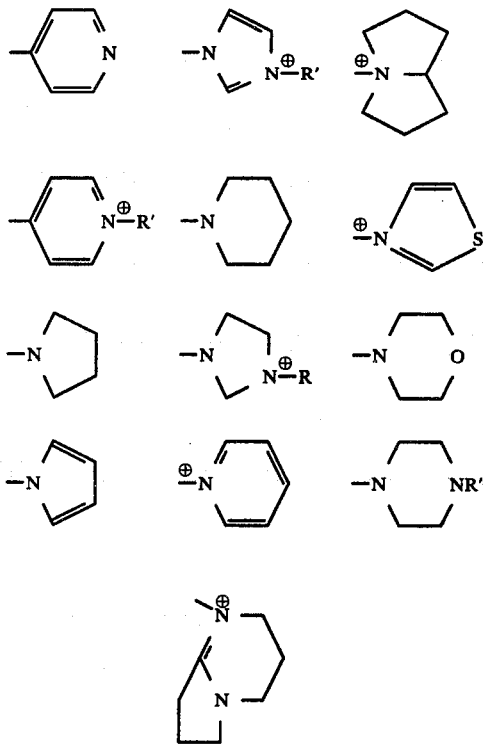

The following specific acyl radicals falling within this class are additionally representative and are preferred:

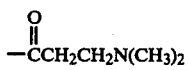

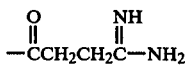

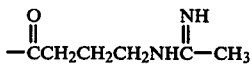

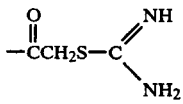

-continued

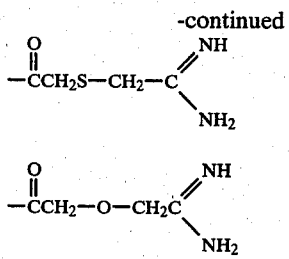

However, it is to be understood that any acyl radical may be employed in the practice of the invention and is to be considered within the scope of the invention.

In the so-called ether embodiments 2. of the present invention (II, above), R is selected from the above-identified acyl radicals wherein the carbonyl moiety,

or more generally,

is deleted; thus R is selected from the following radicals wherein all symbolism has been previously defined:

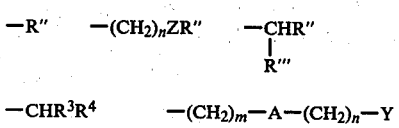

For the ether embodiments 2. as well as in the ester embodiments 1. the most preferred radicals, are (Structure II above), those having a relatively low molecular weight and are hydrophilic. Thus, with respect to the ether embodiments 2. the following radicals are especially preferred and representative: methoxymethyl, hydroxymethyl, methoxyethyl, dimethylaminomethyl, dimethylaminoethyl, methylthioethyl, amidinoethyl, guanidinoethyl and the like. For the ester embodiments 1. the following radicals are representative and preferred: sulfo, phosphono, carbamoyl, methylsulphonyl, sulfamoyl, dimethylsulfomoyl, N-methylcarbamoyl, bromoacetyl, hydroxyacetyl, aminoacetyl, dimethylaminoacetyl, methoxyacetyl, guanylacetyl, guanylthioacetyl, phosphamoyl, phosphonothioyl, thiocarbamoyl, and the like.

In general, the antibiotics of the present invention are prepared by operating upon a fully protected or blocked thienamycin nucleus (III) followed by deblocking:

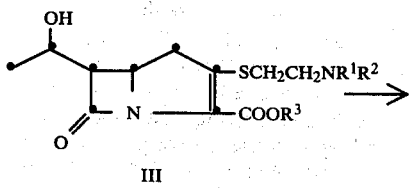

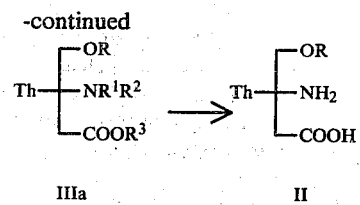

wherein $R^1$ and $R^2$ are conventional N-blocking groups (usually $R^1$ or $R^2$ is hydrogen) and $R^3$ is a convention carboxyl blocking group. The preparation of the N- and carboxyl- blocked species, III, is fully described below and in the Examples. The sole requirement for blocking groups $R^1$, $R^2$ and $R^3$ (or the radical $XR^3$, attached to the carbonyl carbon, wherein X is oxygen or sulphur) is that they do not interfere with the desired reaction and that they are ultimately easily removable to provide II. Thus, the term "blocking group" as utlized herein is employed in the same manner and in accordance with the teachings of U.S. Pat. No. 3,697,515, which patent is incorporated herein by reference.

The preferred N-blocking groups for the starting material III are: carbobenzyloxy, ring-substituted carbobenzyloxy such as o- and p-nitrocarbobenzyloxy, p-methoxycarbobenzyloxy, chloroacetyl, bromoacetyl, phenylacetyl, t-butoxycarbonyl, trifluoroacetyl, bromoethoxycarbonyl, 9-fluorenylmethoxycarbonyl, dichloroacetyl, o-nitrophenylsulfenyl, 2,2,2-trichloroethoxycarbonyl, bromo-t-butoxycarbonyl, phenoxyacetyl; non-acyl protective groups such as alkylidenes, for example, benzylidene, salicylidene, and the like are also of interest.

Suitable blocking esters, $R^3$, for the starting material III include those selected from the following list which is representative and not intended to be an exhaustive list of possible ester group, wherein X is oxygen and $R^3$ is given:

(i) $R^3 = CR^aR^bR^c$ wherein at least one of $R^a$, $R^b$, and $R^c$ is an electron-donor e.g., p-methoxyphenyl, 2,4,6-trimethylphenyl, 9-anthryl,methoxy, $CH_2SCH_3$, tetrahydrofur-2-yl, tetrahydropyran-2-yl, or fur-2-yl. The remaining $R^a$, $R^b$ and $R^c$ groups may be hydrogen or organic substituting groups. Suitable ester groups of this type include p-methoxybenzyloxycarbonyl and 2,4,6-trimethylbenzyloxycarbonyl.

(ii) $R^3 = CR^aR^bR^c$ wherein at least one of $R^a$, $R^b$, and $R^c$ is an electron-attracting group, e.g., benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniumethyl, o-nitrophenyl or cyano. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

(iii) $R^3 = CR^aR^bR^c$ wherein at least two of $R^a$, $R^b$ and $R^c$ are hydrocarbon such as alkyl, e.g., methyl or ethyl, or aryl e.g., phenyl and the remaining $R^a$, $R^b$ and $R^c$ group, if there is one, is hydrogen. Suitable esters of this type include t-butyloxycarbonyl, t-amyloxycarbonyl, diphenylmethoxycarbonyl and triphenylmethoxycarbonyl.

(iv) $R^3 = R^d$, wherein $R^d$ is adamantyl, 2-benzyloxyphenyl, 4-methylthiophenyl or tetrahydropyran-2-yl.

Silyl esters, under this category of blocking groups, may conveniently be prepared from a halosilane or a silazane of the formula $R^4{}_3SiX'$; $R^4{}_2SiX'_2$; $R^4{}_3Si.NR^4{}_2$;

R⁴₃Si.NH.COR⁴; R⁴₃Si.NH.CO.NH.SiR⁴₃; R⁴NH.CO.NR⁴.SiR⁴₃; or R⁴C(OSiR⁴₃); HN(SiR⁴₃)₂ wherein X' is a halogen such as chloro or bromo and the various groups R⁴, which can be the same or different represent hydrogen atoms or alkyl, e.g., methyl, ethyl, n-propyl isopropyl; aryl, e.g. phenyl; or aralkyl, e.g. benzyl groups.

In this connection, it is noted that preferred R³ "blocking groups" include the sub-generic groups defined above as aralkyl, haloalkyl, alkanoyloxyalkyl, alkoxyalkyl, alkenyl, substituted alkyl, or aralkoxyalkyl, and also including alkylsilyl, wherein alkyl has 1-10 carbon atoms. For example, suitable R³ "blocking groups" include benzyl, phenacyl, p-nitrobenzyl, methoxymethyl, trichloroethyl, trimethylsilyl, tributyltin, p-methoxybenzyl, benzhydryl. These blocking groups are preferred since they are generally recognized easily-removable blocking groups in cephalosporin and penicillin art.

In general, the N-, carboxyl-blocked reaction intermediate species III, is prepared by first N-acylating and then derivatizing the carboxyl function; however the blocking reaction may establish R¹/R² and R³ simultaneously in common reaction when permitted by the identity of the chosen blocking groups. Deblocking is preferably conducted as a single step according to procedures well known in the art; however, frequently, depending on the identity of R¹/R² and R³, it is desirable to deblock in separate steps.

Establishment of the blocking groups may be performed by operating upon the free thienamycin, I, or upon a protective derivative thereof such as tris-silylate thienamycin:

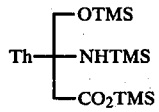

wherein for convenience the previously introduced symbolism for thienamycin is employed and TMS is triorganosilyl such as trimethylsilyl, for example; preparation of such species is fully described in Example 21, below.

The preferred N-blocking groups R¹ and R² are those wherein R¹ is hydrogen and R² is a substituted or unsubstituted carbobenzyloxy radical:

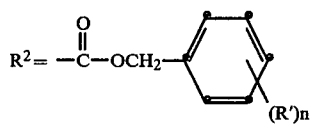

wherein n is 0-2 (n=0, R'=hydrogen) and R⁴⁰ is lower alkoxy or nitro. Another especially preferred N-blocking group is bromo-t-butoxycarbonyl.

The preferred carboxyl blocking group, R³, is benzyl or substituted benzyls, such as p-nitrobenzyl:

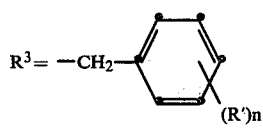

wherein n is 0-2(n=0, R'=H) and R' is loweralkoxyl or nitro.

Thus, the preferred starting material, III, may be depicted by the following:

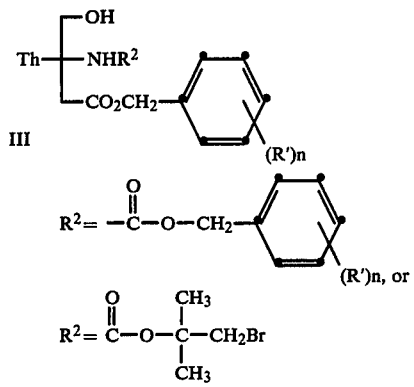

In general, III, is prepared by treating thienamycin in water or a mixture of water and a polar organic solvent such as dioxane in the presence of base with an acyl halide such as carbobenzyloxy chloride. The resulting N-acyl-thienamycin derivative is isolated by conventional techniques. The carboxyl blocking group is conveniently established as a second step; wherein the N-blocked thienamycin is treated with an activated halide such as benzyl bromide in a solvent such as hexamethylphosphoramide or the like at a temperature of from 0° C. to 60° C. for from a few minutes to 4 hours. The resulting N- and carboxyl-blocking species, III, is then converted to intermediate species IIIa, by the process described below. Intermediate species IIIa is deblocked to yield the compounds of the present invention II, by any of several well-known procedures which include hydrolysis and hydrogenation. When the preferred N- and carboxyl-blocking groups are employed, the preferred deblocking procedure is hydrogenation; wherein the intermediate species IIIa, in a solvent such as lower alkanol, is hydrogenated in the presence of hydrogenation catalysts such as Pt, Pd or oxides thereof.

In the preparation of II, the N-protected species (1) may be prepared first:

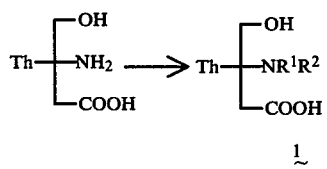

In general, the N-protected species 1 (above) wherein R¹ and R² are H or acyl is prepared by treating thienamycin (I) with an acylating agent, for example, an acyl halide or acyl anhydride such as aliphatic, aromatic, heterocyclic, araliphatic or heterocyclic aliphatic carboxylic acid halide or anhydride. Other acylating agents may also be employed, for example, mixed carboxylic acid anhydrides and particularly lower alkyl esters of mixed carboxylic -carbonio anhydrides; also, carbocylic acids in the presence of a carbodiimide such as 1,3-dicyclohexylcarbodiimide, and an activated ester of a carboxylic acid such as the p-nitrophenyl esters. The acylation reaction may be conducted at a temperature in the range of from about −20° C. to about 100° C.

but is preferably conducted at a temperature in the range of from −8° C. to 25° C. Any solvent in which the reactants are soluble and substantially inert may be employed, for example, polar solvents such as water, alcohols and polar organic solvents in general such as dimethylformamide (DMF), hexamethyl phosphoramide (HMPA), acetone, dioxane, tetrahydrofuran (THF), acetonitrile, heterocyclic amines such as pyridine, ethylacetate, aqueous mixture of the above, as well as halogenated solvents such as methylene chloride and chloroform. The reaction is conducted for a period of time of from about five minutes to a maximum of three hours, but in general, a reaction time of about 0.5 to about one hour is sufficient. The following equation illustrates this process employing a carboxylic acid halide; however, it is to be understood that by substituting a carboxylic acid anhydride or other functionally equivalent acylating agent similar products may be obtained.

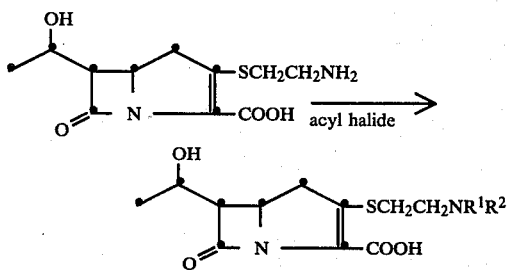

Generally when the above-described acylating reaction employs an acid halide (suitable halides are chloro, iodo or bromo) or anhydride the reaction is conducted in water or an aqueous mixture of a polar organic solvent such as acetone, dioxane, THF, DMF, acetonitrile or the like in the presence of a suitable acceptor base such as NaHCO₃, MgO, NaOH, K₂HPO₄ and the like.

In cases where the acylating reagent is exceedingly water sensitive, it is sometimes advantageous to perform the acylation in a non-aqueous solvent. Triorganosilyl (or tin) derivatives of thienamycin are suitable for this purpose. Silylation of thienamycin proceeds rapidly to give the tris-triorganosilyl derivative, for example, tris-trimethylsilyl thienamycin, Th(TMS)₃:

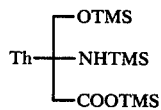

Such derivatives, which are readily soluble in organic solvents, are conveniently prepared by treating thienamycin with an excess of hexamethyldisilazane and a stoichiometric amount of trimethylchlorosilane at 25° C., with vigorous stirring under a N₂ atmosphere. The resulting NH₄Cl is removed by centrifugation and the solvent is removed by evaporation to provide the desired silyl derivative.

In general, the intermediate starting material III is prepared from the N-protected species 1 according to the following scheme:

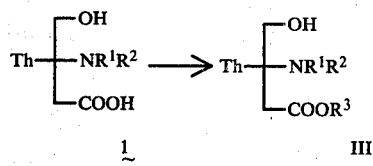

wherein all symbolism is as previously defined. In general, the transformation 1→III is accomplished by conventional procedures known in the art. Such procedures include:

1. Reaction of 1, with a diazoalkane such as diazomethane, phenyldiazomethane, diphenyldiazomethane and the like in a solvent such as dioxane, ethylacetate, acetonitrile and the like at a temperature of from 0° C. to reflux for from a few minutes to 2 hours.

2. Reaction of an alkali metal salt to 1 with an activated alkyl halide such as methyl iodide, benzyl bromide, or m-phenoxybenzyl bromide, p-t-butylbenzyl bromide, pivaloyloxymethyl chloride, and the like. Suitable reaction conditions include solvents such as hexamethylphosphoramide and the like at a temperature of from 0° C., to 60° C., for from a few minutes to 4 hours.

3. Reaction of 1 with an alcohol such as methanol, ethanol, benzyl alcohol, and the like. This reaction may be conducted in the presence of a carbodiimide condensing agent such as dicyclohexylcarbodiimide or the like. Suitable solvent, at a temperature of from 0° C., to reflux for from 15 minutes to 18 hours, include CHCl₃, CH₃Cl, CH₂Cl₂ and the like.

4. Reaction of an N-acylated acid ahydride of 1 prepared by reacting the free acid III with an acid chloride such as ethylchloroformate, benzylchlrooformate adn the like with an alcohol such as those listed in 3. under the same conditions of reaction as given above for 3. The anhydride is prepared by reacting III and the acid chloride in a solvent such as tetrahydrofuran (THF) CH₂Cl₂ and the like at a temperature of from 25° C. to reflux for from 15 minutes to 10 hours.

5. Reaction of labile esters of thienamycin (I) such as the trimethylsilyl ester, dimethyl-t-butylsilyl ester or the like with RX' wherein X' is halogen such as bromo and chloro and R is as defined, in a solvent such as THF, CH₂Cl₂ and the like at a temperature of from 0° C., to reflux for from 15 minutes to 16 hours. For example, according to the following scheme:

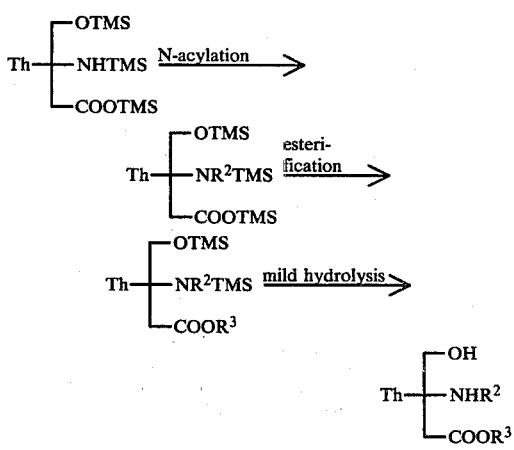

wherein TMS is triorganosilyl such as trimethylsilyl and all other symbolism is as previously defined.

The above-recited schemes of esterification are well known in the related bicyclic β-lactam antibiotic art and indeed in all of general organic synthesis and it is to be noted that there is no undue criticality of reaction parameters in the preparation of the N-acyl and carboxylthienamycin (starting materials III) of the present invention.

In general, the compounds of the present invention are prepared by any of a variety of well-known esterification or etherification reactions (III→IIIa) upon the secondary alcoholic group of Thienamycin in its protected form, III. (The deblocking procedure (IIIa→II) to provide the compounds of the present invention has previously been discussed) Such procedures (III→IIIa) include:

1. For the preparation of ether embodiments of the present invention, the acid catalized reaction of III with a diazoalkane such as diazomethane, phenyldiazomethane, diphenyldiazomethane and the like in an inert solvent such as dioxane, tetrahydrofuran (THF), halohydrocarbons such as $CH_2Cl_2$, ethylacetate and the like in the presence of a catalytic amount of a strong acid or Lewis acid such as toluenesulfonic acid, trifluoroacetic acid, fluoboric acid, boron trifluoride and the like at a temperature of from $-78°$ C. to $25°$ C. for from a few minutes to 2 hours.

2. For the preparation of ether embodiments of the present invention, the reaction of III with an alkylating agent such as active halides, for example, methyliodide, benzylbromide, m-phenoxybenzylbromide, and the like, alkyl sulphonates such as dimethylsulfate, diethylsulphate, methylfluorosulfonate, and the like in the presence of a strong base capable of forming the alcoholate anion of III. Suitable bases include alkali and alkaline earth metal oxides and hydrous oxides, alkali metal alkoxides such as potassium tertiary-butoxide, tertiary amines such as triethylamine, alkali metal alkyls and aryls such as phenyllithium, and alkali metal amides such as sodium amide. Suitable solvents include any inert anhydrous solvent such as t-butanol, dimethylformamide (DMF), THF, hexamethylphosphoramide (HMPA) dioxane and the like at a temperature of from $-78°$ C. to $25°$ C., for from a few minutes to 4 hours.

3. For the preparation of ester embodiments, of the present invention, the reaction of III with any of the above-listed acyl radicals in their acid form. This reaction may be conducted in the presence of a carbodiimide condensing agent such as dicyclohexylcarbodiimide or the like. Suitable solvents include any inert solvent such as $CHCl_3$, $CH_2Cl_2$ DMF, HMPA, acetone, dioxane and the like at a temperature of from $0°$ C. to $60°$ C. for from 15 minutes to 12 hours.

4. For the preparation of ester embodiments of the present invention, the reaction of III with an acyl halide or an acid anhydride, wherein the acyl moiety is described above. Generally, when the above-described acylating reaction employs an acid halide (suitable halides are chloro, iodo or bromo or acid anhydride) the reaction is conducted in an anhydrous organic solvent such as acetone, dioxane, methylenechloride chloroform DMF, or the like in the presence of a suitable acceptor base such as $NaHCO_3$, MgO, triethyleneamine, pyridine, and the like at a temperature of from $0°$ C. to $40°$ C. for from 1 to 4 hours.

Suitable acyl halides and anhydrides include: acetic anhydride, bromoacetic anhydride, propionic anhydride, benzoylchloride, phenylacetyl chloride, azidoacetyl chloride, 2-thienylacetyl chloride, 2-,3- and 4-nicotinyl chloride, p-nitrobenzoyl chloride, 2,6-dimethoxybenzoyl chloride, 4-guanidinophenylacetyl chloride, hydrochloride, methanesulfonyl chloride, dibenzylphosphorochloridate, dimethylthiophosphorochloridate, 2-furoyl ethyl, 2-furoyl ethyl carbonic anhydride, methylchloroformate, bis(p-nitrobenzyl)phosphorochloridate and the like.

5. For the preparation of ester embodiments of the present invention, the reaction of III with a suitably substituted ketene or isocyanate such as ketone, dimethyl ketone, methylisocyanate, methylisothiocyanate, chlorosulfonyl isocyanate and the like. Suitable solvents include dioxane, tetrohydrofuran, chloroform and the like at a temperature of from $-70°$ C. to $60°$ C. for from 15 minutes to 18 hours.

The products of this invention (II) form a wide variety of pharmacologically acceptable salts with inorganic and organic bases; these include, for example, metal salts derived from alkali metal or alkaline earth metal hydroxides, carbonates or bicarbonates and salts derived from primary, secondary or tertiary amines such as monoalkylamines, dialkylamines, trialkylamines, lower alkanolamines, di-lower-alkanolamines, lower alkylenediamines, N,N-diaralkyl lower alkylenediamines, aralkylamines, amino substituted lower alkanols, N,N-di-lower alkylamino substituted lower alkanols, amino-, polyamino- and guanidino-substituted lower alkanoic acids and nitrogen-containing heterocyclic amines. Representative examples include salts derived from sodium hydroxide, sodium carbonate, sodium bicarbonate, potassium carbonate, potassium hydroxide, calcium carbonate, trimethylamine, triethylamine, piperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline, N-methylglucamine and the like. Acid addition salts, e.g., with hydrochloric, hydrobromic, sulfuric, nitric, toluene-p-sulphonic and methane sulphonic acids may also be employed.

The salts can be mono-salts such as the monosodium salt obtained by treating one equivalent of sodium hydroxide with one equivalent of the product (II), also mixed di-salts may be obtained by treating one equivalent of a mono-salt with one equivalent of a different base. Alternatively, salts may be obtained by treating one equivalent of a base having a divalent cation, such as calcium hydroxide, with one equivalent of the product (II). In addition, mixed salts and ester such as those obtained by treating the product (II) with one equivalent of sodium hydroxide and then with one equivalent of lactic acid are also within the scope of this invention. The salts of this invention are pharmacologically acceptable nontoxic derivatives which can be used as the active ingredient in suitable unit-dosage pharmaceutical forms. Also, they may be combined with other drugs to provide compositions having a broad spectrum of activity. In addition, the instant salts and, also, the corresponding ester and amide derivative, have utility as intermediates in preparing the carboxylic acid product illustrated by formula II supra.

The novel Thienamycin derivatives of the present invention are valuable antimicrobial substances which are active against various gram-positive and gram-negative pathogens such as *Bacillus subsilis, Salmonella* schottmuelleri and Proteus vulgaris. Thus, the free acid and especially the salts thereof such as amine and metal salts, particularly the alkali metal and alkaline earth metal salts, are useful bactericides and can be used for removing susceptible pathogens from dental and medical equipment, for separating microorganisms, and for therapeutic use in humans and animals. For this latter purpose pharmacologically acceptable salts with inorganic and organic bases such as those known in the art and used for the administration of penicillins and cephalosporins can be utilized. For example, salts such as alkali metal and alkaline earth metal salts, and primary, secondary and tertiary amine salts can be used for this purpose. These salts can be combined with pharmaceutically acceptable liquid and solid vehicles to form suitable dosage unit forms such as pills, tablets, capsules suppositories, syrups, elixirs and the like which can be prepared in accordance with procedures well known in this art.

The novel compounds are valuable antibiotics active against various gram-positive and gram-negative bacteria and, accordingly, find utility in human and veterinary medicine. The compounds of this invention can therefore be used as antibacterial drugs for treating infections caused by gram-positive or gram-negative bacteria, for example against *Staphylococcus aureus, Escherichia coli, Klebsiella pneumoniae, Bacillus substilis, Salmonella typhosa, Pseudomonas* and *Bacterium proteus.* The antibacterials of the invention may further be utilized as additives to animal feedingstuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The products of this invention may be used alone or in combination as the active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugsar, maize-starch, calcium phosphate, sorbitol or glycine; lubricants for example, magnesium stearate, talc, polyethylene glycol, silica; disintegrants, for example, potato starch or acceptable wetting agents such as sodium luryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or simi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg. of the active ingredient; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution.

In the following Examples, which further illustrate but do not limit the product, process, compositional or method of treatment aspects of the present invention, the compounds of the present invention will be designated by the previously introduced symbol:

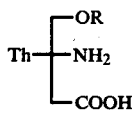

wherein the three functional groups are illustrated.

EXAMPLE 1

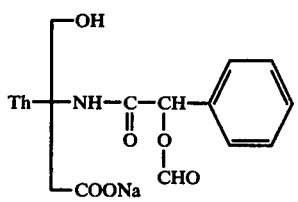

Preparation of N-(O-formyl)-D-mandeloylthienamycin Sodium Salt

To thienamycin (40 mg) in 10 ml. water is added successively at 0° C., 124 mg. $NaHCO_3$, 8 ml. dioxane and then with stirring 1.2 equivalent N-(O-formyl)-1-mandeloyl chloride over a period of one minute. After six minutes total reaction time, the mixture is extracted three times with cold ethyl ether. Electrophoresis of an aqueous portion (0.05 M, pH 7, aqueous phosphate buffer, 50 V/cm., 20 minutes) shows 67% conversion to desired product. The pH is adjusted to 2.2 with 1 M $H_3PO_4$ solution and the solution is extracted three times with ethyl acetate. The ethyl acetate (EtOAc) solution is dried over $MgSO_4$ and extracted twice with two equivalents of $NaHCO_3$ solution. The aqueous extract, lyophilized, contains 164 optical density units (ODU), at 302 nm by uv analysis at pH 7.0, of which 95% is extinguished after treatment with hydroxylamine for one hour. The yield is 53%. Electrophoresis as before shows one spot by bioautograph, 4 cm towards the anode. NMR ($\delta$ $D_2O$) 1.30 (d, J=6 Hz, $\underline{CH_3}$CH); 2.8–3.7 (m, $CH_2$), 4.0–4.5 (m, CH $\beta$-lactam), 4.73, HDO; 5.97 (s, $C_6H_5\underline{C}HOCHO$), 7.53 (s, $C_6H_5$), 8.30 (s, $C_6H_5CHO\underline{C}HO$).

EXAMPLE 2

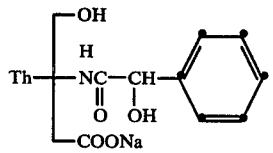

Preparation of N-D-Mandeloylthienamycin Sodium Salt

The title compound is made following the procedure of Example 1, but before EtOAc extraction the aqueous extract was allowed to stand at 25° C. for one hour. Electrophoresis (50 V/cm., 20 min., pH 7, aqueous phosphate, 0.05 M) shows one spot by bioautograph, 4 cm. towards the anode, NMR ($\delta$, $D_2O$) 1.50 (d, J=6 Hz, $CH_3CH$); 2.8–3.8 (m, $CH_2$), 4.2–4.6 (m, CH $\beta$-lactam); 4.96 (s, HDO); 5.40

EXAMPLE 3

N-Propionylthienamycin Sodium Salt

To thienamycin, (25 mg. in 6 ml. water at 0° C.) is successively added 38.6 mg. $NaHCO_3$, 5 ml. dioxane and then with stirring one equivalent of propionic anhydride over a period of 3 min. After 10 min., the mixture is extracted three times with cold ethyl ether. Electrophoresis of the aqueous (aq.) extract (0.05 M, pH 7, phosphate buffer, 50 V/cm., 20 min.) shows no free Thienamycin present. The aq. extract is adjusted to pH 6.8 and contains 600 ODU at 302 nm by uv analysis which is 95% extinguished after treatment with hydroxylamine for one hour. NMR ($\delta$, $D_2O$) 1.42 (m, $CH_2CH_3$, $CH_3CH$); 2.48 (q, $CH_2CH_3$); 2.86–2.90 (m, $CH_2$), 4.30–4.70 (m, CH $\beta$-lactam), 4.86 (HDO).

EXAMPLE 4

N-(Methoxyacetyl)thienamycin Sodium Salt

To thienamycin, (55 mg. in 6 ml. water at 0° C.), is added successively 68 mg. $NaHCO_3$, 6 ml. dioxane and with stirring 1.1 equivalents methoxyacetylchloride over a period of 1.5 minutes. The mixture is stirred an additional 10 minutes. The mixture is extracted three times with cold ethyl ether. Electrophoresis of aq. extract (0.05 M, pH 7 phosphate buffer, 50 V/cm., 20 min.) shows no free Thienamycin present. The aq. extract, adjusted to pH 6.8, contains 105 ODU at 302 nm. by uv analysis, which is 95% extinguished after treatment with hydroxylamine for one hour. NMR ($\delta$, $D_2O$) 1.56 (m, $CHCH_3$), 2.84–3.60 ($CH_2$), 3.72 (s, $OCH_3$), 4.29 (s, $OCH_2$), 4.98 (s, HDO).

EXAMPLE 5

N-(p-Nitrobenzyloxycarbonylthienamycin Lithium Salt

To Thienamycin (220 mg. in 60 ml. water at 0° C.), is added successively, 679 mg. $NaHCO_3$, 60 ml. dioxane and then with stirring 1.1 equivalents p-nitrobenzylchloroformate over a period of 1.5 minutes. The mixture is allowed to react 10 minutes, and is then extracted three times with cold ethyl ether. Electrophoresis (0.05 M, pH 7, phosphate buffer, 50 V/cm., 20 minutes) shows no free Thienamycin present. The aq. extract is adjusted to pH 2.2 with 1 M $H_3PO_4$ solution and extracted three times with EtOAc. The EtOAc extract is dried over $MgSO_4$, filtered and reextracted 0.1 N LiOH, to pH 8.2. The final pH is adjusted to 7.0 with 1 M $H_3PO_4$ and the sample lyophilized. The yield is 205 mg. (54%).

EXAMPLE 6

Preparation of N-(p-nitrobenzyloxycarbonyl)-Thienamycin p-t-butyl benzyl Ester

N-(p-nitrobenzyloxycarbonyl)Thienamycin Li salt, the product of Example 5 (205 mg) in 2 ml. hexamethylphosphoramide (HMPA) is treated for 2.5 hrs. with 0.1625 ml. p-t-butylbenzyl bromide. The starting material is insoluble in HMPA but goes into solution after 30 minutes.

The reaction mixture is diluted with ethyl acetate (EtOAc), washed successively with water, aqueous K₂HPO₄, water, saturated aqueous NaCl, dried over MgSO₄, filtered evaporated and subjected to preparative thin layer chromatography on silica gel; eluting with 1:2 CHCl₃: EtOAc. Yield 160 mg (58%), Rf 0.38, IR (μ film) 2.98 NH and OH 5.63, β-lactam; 5.86 broad ester and urethane; NMR (δ, CDCl₃), 1.24 (s, CHC$\underline{H}$₃, t-butyl), 2.59–3.27 (m, CH₂) 3.83–4.47 (m, CH β-lactam), 5.15 (sOCH₂C₆H₄NO₂), 5.22 (s OCH₂C₆H₄ t-butyl (7.45 and 8.12 (AB quartet, J=8 Hz C₆H₄NO₂)

EXAMPLE 7

Preparation of N-(p-Nitrobenzyloxycarbonyl)Thienamycin m-Phenoxybenzyl Ester

Following the procedure of Example 6, the title compound is prepared when an equivalent amount of m-phenoxybenzyl bromide is substituted for the p-t-butylbenzyl bromide of Example 6, Yield 11%, IR (μ film) 3.0 NH₂, and OH 5.63 β-lactam; 5.86 broad peak ester and urethane; nmr (δ CHCl₃) 1.33 (d CHC$\underline{H}$₃ J=6); 2.60–3.62 (m, CH₂), 7.45 and 8.13 (AB quartet, J=8, C₆H₄NO₂); 7.26 (s C₆H₄OC₆H₅) M.S. m/e 589, 559, 547, 183.

EXAMPLE 8

Preparation of:
1. N-(O-Formyl-D-mandeloyl Thienamycin p-t-butylbenzyl ester
2. N-(O-Formyl)-D-mandeloyl Thienamycin m-phenoxybenzyl ester
3. N-D-Mandeloyl Thienamycin p-t-butylbenzyl ester
4. N-D-Mandeloyl Thienamycin m-phenoxybenzyl ester
5. N-Propionyl Thienamycin p-t-butylbenzyl ester
6. N-Propionyl Thienamycin m-phenoxybenzyl ester
7. N-Methoxyacetyl Thienamycin p-t-butylbenzyl ester
8. N-Methoxyacetyl Thienamycin m-phenoxybenzyl ester.

Following the procedure of Examples 6 and 7, title compounds 1., 3., 5., 7 and 2., 4., 6., 8 are prepared, respectively, when the appropriate N-acyl thienamycin starting material from Examples 1–4 replaces, in equivalent amount the N-(p-nitrobenzyloxycarbonyl) thienamycin starting material of Examples 6 and 7, respectively.

EXAMPLE 9

Preparation of N-(p-Methoxybenzyloxycarbonyl)thienamycin p-t-Butylbenzyl Ester

Step A: N-(p-methoxybenzyloxycarbonyl)thienamycin Sodium salt (I) and Lithium salt (II)

To Thienamycin (20 mg.) in 5 ml. water at 0° C. is added 105 mg. NaHCO₃ (20 equivalents), 5 ml. dioxane, and then, dropwise with stirring over 1 min. ten equivalents of p-methoxybenzyl chloroformate. After 15 min. the pH is adjusted to 7.5 with 1 M H₃PO₄ and the solution extracted 3× with ether. The aqueous portion is then adjusted to pH 2.2 at 0° C. and extracted 3× with ethylacetate (EtOAc). The EtOAc is dried quickly with MgSO₄, filtered and extracted with a few ml. water containing 6.3 mg. NaHCO₃. The aqueous extract, lyophilized, contains 172 ODU at 303 nm by UV analysis in H₂O at pH 7.0, which is 95% extinguished after treatment with hydroxlamine for one hour. The yield is 16 mg. Electrophoresis (50 v/cm, 20 min., pH 7 aqueous phosphate, 0.05 M) shows one spot by bioautograph, 4 cm towards the anode. NMR (δ, D₂O): 1.49 (d, J=6 Hz CH₃CH); 2.8–3.7 (m,CH₂); 3.99 (s, OMe); 4.0–4.6 (m, β-lactam CH); 4.92 (s, HDO); 5.20 (s, OCH₂); 7.13 (d, J=8 Hz C₆H₄).

The lithium salt II is made in the same way, but extracting the EtOAc solution with 0.1 N LiOH to pH 7.8 (instead of aqueous NaHCO₃), and lyophilizing. The spectral and electrophoretic properties of II are the same as those of I.

Step B: N-(p-methoxybenzyloxycarbonyl)thienamycin-p-t-Butylbenzyl Ester

The lithium salt of Step A (37 mg.) in 0.4 ml. hexamethylphosphoramide (HMPA), is treated for 2 1/5 hours with 0.033 ml. p-t-butylbenzyl bromide. The lithium salt is insoluble in HMPA but goes into solution after 15 minutes reaction time.

The reaction mixture is diluted with EtOAc, washed successively with water twice, aqueous K₂HPO₄, water and brine, dried with MgSO₄, filtered, evaporated and subjected to preparative layer chromatography on silica gel, eluting with 1:2 CHCl₃-EtOAc, affording 47 mg. pure II, Rf=0.3. IR (μ, film): 3.0, NH; 5.63, β-lactam; 5.87 broad, ester and urethan. NMR (δ, CDCl₃): 1.21 (s, Me and t-butyl); 2.6–3.6 (m, CH₂); 3.72 (s, OMe); 3.8–4.4 (m, β-lactam CH);

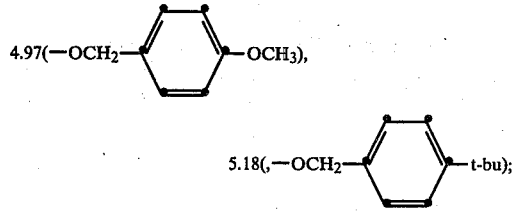

6.84 and 7.20 (AB quartet, C₆H₄ OMe); 7.32 (s, C₆H₄-t-Bu). MS: 582, 538, 496.

EXAMPLE 10

Preparation of N-(p-methoxybenzyloxycarbonyl)thienamycin Benzhydryl Ester

To Thienamycin (23.5 mg.) in 5 ml. water is added successively 4 ml. dioxane, 62 mg. NaHCO₃, and then, in portions at 0° C. with stirring, 4 equivalents p-methoxybenzyl chloroformate over 4 minutes. After ten minutes total reaction time, the pH is adjusted to 7.0 with 1 M H₃PO₄ and the mixture extracted three times with ether. Electrophoresis of the aqueous portion (0.05 M pH 7 aqueous phosphate buffer, 50 V/cm, 20 minutes) shows 50% conversion to N-(p-methoxybenzyloxycarbonyl)thienamycin.

The aqueous solution is brought to pH 2.2 with 1 M H₃PO₄ at 0° C. and extracted 3× with EtOAc. The EtOAc solution is treated with 50 mg. diphenyldiazomethane, evaporated and taken up in CH₃CN. More diphenyldiazomethane is added to a persistent purple color. After 0.5 hour the solution is evaporated and chromatographed on silica gel, eluting with 1:2 CHCl₃-EtOAc, affording 10 mg. pure title compound Rf 0.25. IR (μ, film): 3.0, NH; 5.63, β-lactam; 5.85, 5.89, ester and urethan. NMR (δ, CDCl₃); 1.23 (s, OH); 1.30 (d, J=6 Hz, CH₃CH); 2.6–3.6 (m, CH₂); 3.78 (s, OMe);

5.02 (s OCH₂); 3.8–4.4 (m, β-lactam CH); 6.9 and 7.35 (AB quartet, J=9 Hz, C₆H₄), 7.3s CHPh₂.

EXAMPLE 11

Preparation of N-(o-Nitrobenzyloxycarbonyl)Thienamycin Benzyl Ester

Step A: N-(o-Nitrobenzyloxycarbonyl)thienamycin Sodium Salt

To Thienamycin (43 mg.) at 0° C. is added 10 ml. 1:1 tetrahydrofuran (THF:Water). The mixture is rapidly stirred while 102 mg. NaHCO₃ (10 equivalents) is added, and then, dropwise with stirring over 2 minutes, four equivalents of o-nitrobenzylchloroformate is added. After 30 minutes, the pH is adjusted to 7 with aqueous 25% H₃PO₄ and the solution extracted three times with ether. The aqueous layer is evaporated at 25° C., in vacuo and is then adjusted to pH 2.2 at 0° C. Solid NaCl is added, and the cold acidic solution is extracted 3× with cold EtOAc. The EtOAc extracts are combined and quickly back-washed with cold brine; dried with MgSO₄, filtered and back extracted with 10 ml. of water containing 1.75 equivalents of solid NaHCO₃. The extract is lyophilized in vacuo at 25° C. to provide the title compound.

Step B: N-(o-Nitrobenzyloxycarbonyl)Thienamycin Benzyl Ester

The product of Step A in 7.5 ml. EtOAc (from the pH 2.2 extraction) is treated with an excess of phenyldiazomethane (4 ml. of solution comprising 20 mg./ml. ether) at 4° C. for 2.3 hours. The mixture is concentrated to wet residue at 20° C. under reduced pressure. The desired compound is isolated by thin layer chromatography, EtOAc; ether (9:1) to afford 17.5 mg. of N-(o-Nitrobenzyloxycarbonyl)thienamycin benzyl ester.

EXAMPLE 12

Preparation of N-(o-Nitrobenzyloxycarbonyl)Thienamycin p-methoxy Benzyl Ester

To N-(o-Nitrobenzyloxycarbonyl)thienamycin (70 mg.) in 8 ml. of EtOAc is added 4 ml. of p-methoxyphenyldiazomethane (9 mg./ml. acetonitrile) at 4° C. The mixture is stirred for 1.5 hours at 4° C. and is then concentrated to a wet paste under reduced pressure at 20° C. The title compound (42 mg.) is isolated by thin layer chromatography on silica gel, eluting with EtOA:ether (9:1).

EXAMPLE 13

Preparation of N-(o-nitrobenzyloxycarbonyl)thienamycin p-Bromo-phenacyl Ester

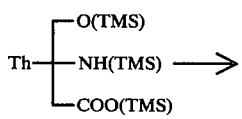

I

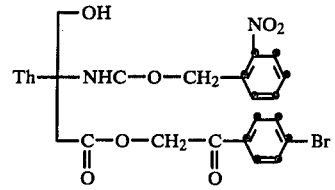

II

[wherein TMS=trimethylsilyl]

To Th(TMS)₃, I, (24 mg.), which is prepared according to Example 17, in 0.8 ml. dry THF is added 23 mg. o-nitrocarbobenzyloxy chloride, followed by 0.015 ml. of triethylamine. After vibro-mixing for 30 minutes at 25° C., the mixture is concentrated to a pasty residue in a stream of dry N₂, and is washed 3× with petroleum ether. The residue is suspended in 1 ml. of dry THF and p-bromophenacylbromide (14 mg.) is added followed by 0.03 ml. triethylamine. After vibro-mixing for 30 minutes at 25° C., the mixture is evaporated to dryness in vacuo at 20° C. The residue is dissolved in EtOAc (2 ml.) and shaken with 0.3 ml. of pH 4 buffer for 5 minutes. The organic layer is dried over MgSO₄, filtered, evaporated to a pasty residue and the desired product is isolated (44 mg.) by preparative thin layer chromatography on silica gel, eluting with EtOAc:CHCl₃ (7:3).

EXAMPLE 14

Preparation of N-(Trichloroethoxycarbonyl)thienamycin Benzyl Ester

Step A: N-(Trichloroethoxycarbonyl)Lithium Salt

To Thienamycin (40 mg.) in 18 ml. 1:1 THF-H₂O at 0° C. is added while stirring 225 mg. (15.2 equivalents) NaHCO₃, and then, dropwise with stirring over 2 min., 1.8 equivalents of trichloroethylchloroformate dissolved in 0.6 ml. THF. After 6 minutes the pH is adjusted to 7.2 with aqueous 25% H₃PO₄ and the solution extracted with ether. The aqueous portion after removing any entrained ether in vacuo is then brought to pH 2.5 at 0° C. and extracted with cold EtOAc. The ethyl acetate extracts are combined, quickly backwashed with cold brine, dried with anhydrous MgSO₄, filtered and back extracted with 0.01 m LiOH to pH 6.8. The aqueous extract is freed from any EtOAc in vacuo and lyophilized. The residual product contains 936 ODu (39.7%) by uv analysis at 302 nm which is 90% extinguished after treatment with hydroxylamine for one hour in 0.05 M phosphate buffer (pH 7). The yield is 32 mg. Electrophoresis (50 volts/cm. 20 min., pH 7 aq. phosphate 0.05 M) exhibits one zone by bioautograph (MB 108, *staph. aureus*), 2.4 cm toward the anode. Liquid chromatography C₁₈ Bondapak (Waters Assoc.) in aqueous 10% THF exhibits one main peak free of any unreacted Thienamycin.

Step B: N-(Trichloroethoxycarbonyl)thienamycin Benzyl Ester

The compound of Step A (32 mg.) in 2 ml. dry distilled DMF containing 7% HMPA (dry, pH 6.3), is treated with 0.015 ml. benzyl bromide for 2 hours at 15° C. (allowing the contents to warm up to 25° C. during the course of the reaction). The reaction mixture is diluted with EtOAc, washed successively with cold H₂O, 1% aqueous NaHCO₃, water and cold saturated aqueous NaCl, dried with MgSO4, filtered, evaporated and subjected to preparative thin layer chromatography on silica gel, eluting with 1% CH3CN in EtOAc to afford 10 mg. of the title compound, Rf=0.63; IR (μ CHCl3) 5.63, β-lactam; 5.78 and 5.88 broad ester and urethane. NMR (δ CDCl3) 1.35 (d, Me); 2.8–3.7 (m CH2); 3.51 and 4.27 (dd, J=6 Hz, β-lactam CH); 4.79 (s, OC̲H2CCl3) 5.42 s(OC̲H2C6H5); and 7.41 (m, C6H5).

EXAMPLE 15

Preparation of N-Bromoacetyl thienamycin Methyl and Benzyl Esters

Step A: N-Bromoacetyl thienamycin

To a cooled solution of thienamycin (28.8 mg.) and sodium bicarbonate (0.3 g.) in 10 ml. of water and 8 ml. of dioxane is added with stirring a solution of 0.25 g. of bromoacetic anhydride in 2 ml. dioxane over a period of 20 minutes. The pH is maintained at 8.0. The mixture is stirred for an additional 5 minutes then layered with 10 ml. of ether and the pH adjusted to 7 by the additional of 8% phosphoric acid. The ethereal layer is separated and the aqueous layer is extracted twice again with ether. The aqueous layer is evaporated under reduced pressure to 0.5 ml., diluted to 2 ml. with water and put on 50 ml. of XAD-2 resin. The column is eluted with water. The first 80 ml. is discarded, then the next 100 ml. is collected. The solvent is changed to 10% THF and an additional 100 ml. collected. The combined eluates are adjusted to pH 7, evaporated to 5 ml. under reduced pressure, then freeze-dried to give the sodium salt of N-bromoacetyl thienamycin in 60% yield. UV $\lambda_{max}$ 302 mμ.

Step B: N-Bromoacetyl thienamcyin Methyl and Benzyl Esters

An aqueous solution of the sodium salt is layered with ethyl acetate at 0° C. and adjusted to pH 2. The ethyl acetate phase is separated and the aqueous phase is extracted with ethyl acetate. The combined ethyl acetate solutions are dried over MgSO4 and then treated with a solution of diazomethane. The solvents are evaporated and the residue chromatographed on a silica gel plate. Rf 0.11 in 2:1 ethyl acetate-chloroform. m.p. 118°–120° C. Mass spectrum shows M+ at m/e 406 and significant fragments at m/e 362, 320, 183, and 164.

The corresponding benzyl ester is prepared in a similar way from phenyldiazonemethane. m.p. 142°–3° C. Ir: 5.65μ, 5.89μ and 6.1μ. Mass spec. M+ m/e 482 also m/e 438, 316, 259 and 164.

EXAMPLE 16

Preparation of N-(Bromo-t-Butoxycarbonyl)thienamycin p-Bromophenacyl Ester

Step A: Preparation of N-Bromo-t-Butoxycarbonyl-O-TMS-Thienamycin-TMS Ester

Th(TMS)3 (16 mg.) is dissolved in 0.4 ml. of dry tetrahydrofuran to which is added 20 μl (28 mg., 0.13 mmol) of bromo-t-butylchloroformate (b.p. 35°/0.9 mm) and 8 μl (5.67 mg., 0.057 mmole) of triethylamine (redistilled from BaO). The mixture is shaken at 25° C. for 20 min. Evaporation of solvent and excess reagents gives crude desired product. UV $\lambda_{max}^{CH3CO2CH2CH3}$ 320 nm (E9,000).

Step B: Preparation of N-(Bromo-t-Butoxycarbonyl)thienamycin

The product of Step A (3 mg.) is dissolved in 0.5 ml. of ph 7 phosphate buffer and 0.1 ml. of tetrahydrofuran and the solution left at 25° C., for 20 minutes. The solution is then passed down a column (5 ml.) of Dowex 50×8 (Na+ form) and the eluate fractions monitored by U.V. The correct fractions are combined and freeze dried to yield the desired product. UV $\lambda_{max}^{buffer}$ 304 nm (ε=9,300); electrophoresis at 50 V/Cm. 20 min in pH 7.0 buffer shows a single bioactive zone which moves 31.5 mm towards the anode.

Step C: Preparation of N-(Bromo-t-Butyoxycarbonyl)thienamycin p-Bromophenacyl Ester The product of Step B (13 mg. 0.022 mmole) is dissolved in 0.4 ml. of tetrahydrofuran. To this solution is added p-bromophenacyl bromide (9.6 mg., 0.035 mmol) and 20 μl (14.4 mg., 0.14 mmole) of triethylamine. The mixture is shaken at 25° C. for 30 min. and then evaporated to dryness. Ten ml. of ether is added to the residue and the mixture treated with 0.2 ml. of 0.1 M pH 7.0 phosphate buffer.

The organic layer is separated, dried over sodium sulfate, concentrated to 0.5 ml. and applied to two 20×20 cm., 250μ silica gel GF tlc plates which are developed with 20% ethyl acetate in chloroform. (Rf=0.65) the desired product (6.7 mg.) is isolated in 42% yield.

EXAMPLE 17

Preparation of N-Benzyloxycarbonyl thienamycin and N-Benzyloxycarbonyl Benzylcarbonic Acid Anhydride

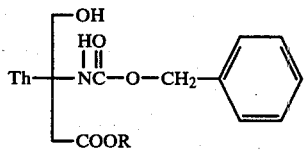

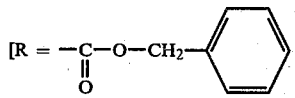

A solution of 16.6 mg of Thienamycin in 4 ml. of 0.05 M pH 7 phosphate buffer and 2 ml. of dioxane in a 3-necked flask fitted iwth a stirrer, thermometer, pH electrode and the delivery tip of an automatic titrator is cooled to −8° C. in a methanol-ice bath. The pH is brought to 8.2 by the addition of 0.2 N sodium hydroxide in 50% aqueous dioxane and a solution of 0.015 ml. of carbobenzyloxy chloride in 2 ml. of chloroform is added. The mixture is stirred at −6° C., pH 8.2, for ten minutes, then layered with ether and the pH adjusted to 7 by the addition of N hydrochloric acid. The layers are separated by centrifufation and the aqueous phase is extracted twice again with ether. The aqueous phase is layered with ethyl acetate and acidified to pH 2. The ethylacetate is separated and the aqueous layer is extracted again with ethyl acetate. The combined ethyl acetate layer is washed with saturated sodium chloride solution, dried over magnesium sulfate and filtered. The filtrate is stirred with water and the pH brought to 7 by the addition of dilute sodium bicarbonate solution. The aqueous phase is separated and freeze dried giving the sodium salt of N-benzyloxycarbonyl Th. Weight 10 mg (46%). The UV spectrum, $\lambda_{max}$ 303 mμ, E% 147 (E 6,290) indicates about 80% purity. Electrophoresis at 50 V/cm. for 20 minutes at pH 7 followed by bioautograph on *S. aureus* gives a zone of inhibition at +2.5 cm.

The ethereal extracts of the reaction mixture contain the desired product N-benzyloxycarbonyl thienamycin benzyl carbonic acid anhydride. UV $\lambda_{max}$ 335 mμ.

EXAMPLE 18

Preparation of N-Benzyloxycarbonyl thienamycin Benzyl Ester

The N-Benzyloxycarbonyl thienamycin [Example 17], in EtOAc is carried through the procedure of Example 17, except that an equivalent amount of phenyldiazomethane is added to the dried EtOAc solution from the pH 2 extraction and the solution left at 4° for 2 hours. Evaporation to dryness yields crude N-benzyloxycarbonylthienamycin benzyl ester which is isolated by thin layer chromatography $R_f$ 0.24 3:1 ethyl acetate chloroform. It crystallizes from ether. IR 5.63μ (lactam carbonyl); shoulder 5.8μ (ester); 5.88μ (urethane carbonyl). UV, dioxane, $\lambda_{max}$ 318 mμ, E% ($\epsilon$=10,900) m/e M+ 496.

EXAMPLE 19

Preparation of N-Carbomethoxy thienamycin p-pivaloyloxybenzyl Ester

Step A: N-Carbomethoxy thienamycin

Thienamycin (49 mg., 148 μmol) is dissolved in 0.05 M pH 7 phosphate buffer (14 ml.) and cooled in an ice bath. With stirring the pH is adjusted to 8.2 using an automatic burette. A solution of methyl chloroformate (46 μl, 600 μmol) in p-dioxane (580 μl) is added at once to give a homgeneous solution. Subsequently, the pH is maintained at 8.2 using the automatic burette. After 10 min., the solution is adjusted to pH 7 using dilute phosphoric acid solution and washed three times with an equal volume of diethyl ether. The aqueous solution is then concentrated to 4.5 ml. and chromatographed on an XAD-2 resin column. The product is eluted (after water elution) with an aqueous 5% tetrahydrofuran solution and is freeze-dried to give 28.9 mg. of product. UV (pH 7 phosphate buffer 0.1 N). $\lambda_{max}$ 303 nm (e 6,450) Electrophoresis (20 min., 0.1 N pH 7 phosphate buffer, 50 V/cm mobility 3.5 cm to cathode.

Step B: N-Carbomethoxy thienamycin p-pivaloyloxybenzyl Ester

Following the procedure of Example 16, Step C, and substituting in equivalent amounts: N-carbomethoxy thienamycin (as its sodium salt) and p-pivaloyloxybenzyl bromide there is obtained N-carbomethoxy thienamycin p-pivaloyloxybenzyl Ester.

EXAMPLE 20

Preparation of N-Benzenesulfonyl thienamycin 2-Methyl-2-propen-1-yl Ester

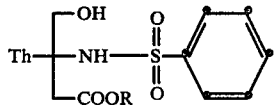

-continued

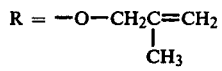

Step A: N-Benzenesulfonyl thienamycin

Thienamycin (52 mg. 148 μmol) is dissolved in pH 7 0.1 N phosphate buffer (25 ml.) and magnetically stirred in an ice bath. The pH is adjusted to 8.2 with 2.5 N NaOH using an automatic dispensing burette and benzenesulfonyl chloride (227 μl, 226 μmol) in 500 ml. p-dioxane added at once. The pH is maintained at 8.2 (using the automatic burette) for 30 min. and then adjusted to pH 7.0 with dilute aqueous phosphoric acid. The reaction solution is concentrated to 15 ml. and chromatographed on XAD-2 resin (50 cc). The column is eluted with water, then with 10% aqueous tetrahydrofuran which elutes the product. The 10% aqueous tetrahydrofuran eluate is concentrated to ⅓ volume and freeze-dried to give 28 mg. Electrophoretic mobility of the product (50 v/cm, 20 min., pH 7 0.05 N phosphate buffer) is 3.5 cm towards the cathode. $\lambda_{max}$ 303 (3,650) in pH 7 0.1 N phosphate buffer).

Step B: N-Benzenesulfonyl thienamycin 2-Methyl-2-propen-1-yl Ester

Following the procedure of Example 24 and substituting in equivalent amounts N-Benzensulfonyl thienamycin (as its sodium salt) and 2-methyl-2-propen-1-yl chloride for the N-azidoacetyl thienamycin sodium salt and p-t-butylbenzyl bromide respectively, the title compound is obtained.

EXAMPLE 21

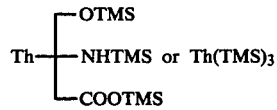

TMS = trimethylsilyl

Preparation of Silylated-Thienamycin

Thienamycin (80.0 mg) is suspended in 40 ml. tetrahydrofuran (THF) and under a $N_2$ atmosphere and is concentrated to 10 ml.; hexamethyldisilazane (1.0 ml.) and trimethylchlorosilane (300 μl) is added. The mixture is reacted for 20 minutes at 25° C. with vigorous stirring. The suspension is then centrifuged to remove ammonium chloride. The decantate is evaporated to an oil under a nitrogen stream for future reaction.

EXAMPLE 22

Preparation of N-(p-Nitrobenzyloxycarbonyl)-Thienamycin(p-Nitrobenzyl)Ester

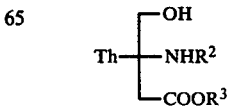

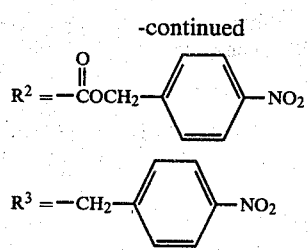

A mixture of p-nitrobenzyloxycarbonyl-Thienamycin-lithium salt (295 mg.) (from Example 5) and 0.4 g of p-nitrobenzyl bromide in 3 ml. of hexamethylphosphoramide is stirred for 3 hours at 25° C. The solution is diluted with 50 ml. of ethyl acetate and extracted successively with water (3×), pH 7 phosphate buffer and saturated sodium chloride solution. The organic phase is dried over magnesium sulfate and evaporated to 5 ml. causing the product to crystallize. The crystals are collected and washed with ethyl acetate, yielding 160 mg. of N-p-nitrobenzyloxycarbonyl-Thienamycin-p-nitrobenzyl ester, m.p. 168°–170° C. NMR (CHCl$_3$) 1.35 [(d), J=6 Hz], 4.0–4.3 and 2.8–3.5 (m), 5.16 [(s), (carbamate OCH$_2$)]; 5.24 (AB quartet, J=14) 7.42(d), 7.56(d), 8.16(d) (J=9, aromatic) IR 5.65µ (lactam C=O)

EXAMPLE 22a

Preparation of N-Bromo-t-butyloxycarbonyl Thienamycin Sodium Salt

Method A:

Thienamycin (190 mg.) dissolved in 15 ml. 0.1 M pH 7.0 phosphate buffer and 15 ml. dioxane is kept at 0° C. The solution is adjusted and maintained between pH 8.5–9.0 with 1 N NaOH while 480 mg of bromo-t-butyl chloroformate is added to the solution during a period of 5 minutes. The mixture is stirred for 30 min., then is neutralized to pH 7.0 with 1 N HCl and extracted with ether. The aqueous layer is separated, concentrated to 10 ml. and chromatographed on a Dowex-50×8 (Na form) column (1.5″×10″) which is eluted with H$_2$O to give 113 mg of the desired product. Lyophilization of the solution gives solid product.

Method B:

Thienamycin (95 mg) in 10 ml. 0.1 M phosphate buffer and 10 ml. dioxane is kept at 0° C. The solution is adjusted and maintained between pH 8.5–9.0 while 240 mg of bromo-t-butyl chloroformate is added. The mixture is stirred for 30 minutes, then is acidified to pH 2.0 with H$_3$PO$_4$. The acidified solution is extracted with 2×25 ml. ethylacetate. The organic layer is separated and back extracted with 10 ml. NaHCO$_3$ solution which contains 30 mg of NaHCO$_3$. The aqueous layer containing 30 mg. of the desired product is lyophilized to give solid product. Nmr (60 MHz, D$_2$O): δ 1.26(d), 1.60(s), 2.65–3.50(m), 3.70(s), and 3.90–4.20(m). UV $\lambda_{max}^{D_2O}$ 303 nm.

Preparation of N-Bromo-t-butyloxycarbonyl Thienamycin p-Nitrobenzyl Ester

The lyophilized N-bromo-t-butyloxycarbonyl-thienamycin sodium salt (100 mg.) is stirred at 25° C., with p-nitrobenzyl bromide (300 mg.) in 2 ml. hexamethylphosphoramide for 1 hour. The mixture is diluted with 10 ml. ethylacetate then is washed thoroughly with water. The organic layer is separated, dried over Na$_2$SO$_4$ and chromatographed on two 250µ silica gel GF TLC plates using ethylacetate as solvent (R$_f$ 0.45) to give 50 mg. of the desired product. IR (CDCl$_3$): 1777 (β-lactam) and 1711 cm$^{-1}$ (ester); UV $\lambda_{max}^{EtOH}$ 270 nm and 322 nm; NMR (CDCl$_3$, 60 MHz): δ 1.38(d), 1.58(s), 2.60–3.80(m), 3.78(s), 3.90–4.20(m), 5.30(s), 7.55(d) and 8.30 ppm (d).

EXAMPLE 23

Preparation of O-Methyl-Thienamycin

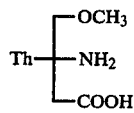

Step A:
O-Methyl-N-(p-Nitrobenzyloxycarbonyl)-Thienamycin-(p-Nitrobenzyl)-Ester

To a solution of 135 mg. of N-p-nitrobenzyl-oxycarbonyl-Thienamycin-p-nitrobenzyl ester in 50 ml. of methylene chloride at 0° C. is added with vigorous stirring 0.5 ml. of 0.006 M fluoboric acid in ether-methylene chloride (3:1), immediately followed by 10 ml. of a cooled solution of 0.6 M diazomethane in methylene chloride. The diazomethane is decolorized in one minute. The solution is extracted with 10 ml. of 0.1 N pH 7 phosphate buffer, dried and evaporated to a small volume. The solution is applied to two 8″×8″ 1000µ silica gel plates which are developed with 3:1 ethylacetate-chloroform. The band at 3–4.5 cm yields 12 mg. of recovered starting material. The band at 6–8 cm yields 20 mg. of crystalline O-methyl-N-(p-nitrobenzyloxycarbonyl)-Thienamycin-(p-nitrobenzyl)ester. m.p. 172°–174° C. MS m/e 600 (M+), 568, 542, 500, 447, 389, 304 and 59.

Step B: O-Methyl-Thienamycin

A solution of 20 mg. of O-methyl-N-p-nitrobenzyl-oxycarbonyl-Thienamycin-p-nitrobenzyl ester in 2 ml. of tetrohydrofuran and 1 ml. of ethanol is hydrogenated at 50 psig, 23° C. in the presence of 20 mg. of platinum oxide for 2½ hours. The catalyst is filtered and 1 ml. of 0.1 N pH 7 phosphate buffer is added to the filtrate. The solution is evaporated under reduced pressure to 2 ml. and the mixture is taken up in 5 ml. of water and 5 ml. of ethylacetate and centrifuged. The ethylacetate layer is removed and the aqueous layer is extracted again with ethylacetate and with ether and then filtered through Celite. The aqueous solution is applied to a column (20 ml.) of XAD-2 resin. The column is first eluted with water and then with 10% tetrahydrofuran. The tetrahydrofuran eluate is concentrated and lyophilized giving substantially pure O-methyl-Thienamycin.

EXAMPLE 24

Preparation of Thienamycin O-Phosphate Ester

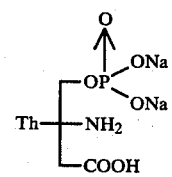

Step A:

To a solution of N-(p-nitrocarbobenzyloxy)-Thienamycin-(p-nitrobenzyl)-Ester (50 mg.) in 5 ml. THF at 3° C. is added 30 mg. of dibenzyl phosphorochloridate followed by 14 μl of triethylamine. The mixture is stirred at 25° C. for 2 hours. whereupon the THF is removed in vacuo. The residue is taken up in methylene chloride and washed with water. The methylene chloride solution is dried over magnesium sulfate and evaporated. The residue is chromatographed on silica gel yielding O-dibenzylphophoryl-N-benzyloxycarbonyl-Thienamycin benzyl ester.

Step B:

A solution of the above product (20 mg.) in 10 ml. of 80% aqueous dioxane containing 8 mg. of $NaHCO_3$ is hydrogenated in the presence of 20 mg. of 5% Pd on charcoal catalyst for 6 hours. The catalyst is removed by filtration and the filtrate evaporated to 2 ml. The solution is extracted twice with methylene chloride then concentrated and freeze dried, leaving the product Thienamycin O-phosphate disodium salt.

EXAMPLE 25

Preparation of O-(Methylcarbamoyl)-Thienamycin

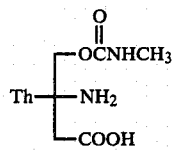

A solution of N-(p-nitrobenzyloxycarbonyl)-Thienamycin-(p-nitrobenzyl) ester (20 mg.) and methylisocyanate (20 mg.) in methylene chloride (5 ml.) is stirred at 23° C. for 18 hours. The solvent is evaporated and the residue extracted with hexane. The hexane insoluble residue is chromatographed on silica gel giving substantially pure O-(Methylcarbamoyl)-N-p-nitrobenzyloxycarbonyl-Thienamycin-p-nitrobenzyl ester. Following the hydrogenation procedure of Example 4, Step B, the product is obtained when the indicated substitution is made.

EXAMPLE 26

Preparation of O-(Methoxymethyl)-Thienamycin

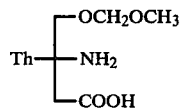

Step A:

A solution of 58 mg. of p-nitrobenzyloxycarbonyl-Thienamycin-p-nitrobenzyl ester in 5 ml. and 1 ml. of HMPA is cooled to −78° C. To this solution is added with stirring a 2 N solution of phenyllithium (0.1 ml.) immediately followed by the addition of 0.2 ml. of methylchloromethyl ether. The mixture is allowed to warm to 25° C. during a period of one hour. Methylene chloride (25 ml.) is added and the solution is extracted with 0.1 N, pH 7, phosphate buffer (25 ml.), and water 4×25 ml. The methylenechloride solution is evaporated and the residue is triturated with hexane. The hexane insoluble residue is chromatographed on silica gel yielding O-methoxymethyl-N-(p-nitrobenzyloxycarbonyl-Thienamycin-(p-nitrobenzyl)ester.

Step B:

Following the hydrogenation procedure of Example 4, Step B, the title compound is obtained when the indicated substitution is made.

EXAMPLE 27

Preparation of O-Methyl-Thienamycin

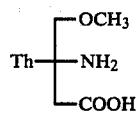

Step A:
O-Methyl-N-Benzyloxycarbonyl-Thienamycin-Benzyl Ester

A solution of 5 mg. of N-benzyloxycarbonyl Thienamycin benzyl ester (Example 18) in 0.3 ml. of methylene chloride is cooled to 0° C. and 0.1 ml. of a 0.006 M solution of fluoboric acid in 5:1 ether-methylene chloride is added, followed immediately by 0.5 ml. of 0.1 M diazomethane is methylene chloride. The solution is decolorized in 1 minute. The mixture is stirred with ether and pH 7 phosphate buffer and the ethereal phase is evaporated. The residue is chromatographed on 2×8" 250μ silica plates in 35% ethyl acetate-chloroform. The band at $R_f$ 0.5 is eluted with ethyl acetate. Measurement of the U.V. absorbance at 318 mμ shows a 13% recovery of the initial optical density. Mass spectrum analysis shows m/e M+ 510 and fragments at m/e 410, 59, 333 and 478 characteristic of O-methyl-N-benzyloxycarbonyl-Thienamycin benzyl ester.

Alternate Step A:
O-Methyl-N-Benzyloxycarbonyl-Thienamycin-Benzyl Ester

A solution of N-benzyloxycarbonyl-Thienamycin-benzyl ester (5 mg.) in 0.2 ml. dry THF is cooled to −78° C. To this solution is added 5 μl of phenyllithium solution (2 N) followed immediately by 1 μl of methylfluorosulfonate. The mixture is stirred at −78° C. for 20 minutes and is then diluted with 2 ml. of ether and extracted with 2 ml. of 0.01 N pH 7 phosphate buffer. The ethereal layer is evaporated and the residue is chromatographed on a 2"×8" thin layer silica gel plate in 1:1 ethylacetate-chloroform. The band at $R_f$=0.63 is isolated giving the desired product, O-Methyl-N-benzyloxcarbonyl-Thienamycin-benzyl ester.

Step B: O-Methyl-Thienamycin

A solution of 0.2 mg. of the above product in 0.5 ml. dioxane containing 0.3% acetic acid is hydrogenated for 3 hours in the presence of 2 mg. of palladium oxide catalyst at 45 psig and 25° C. The mixture is shaken with 4 ml. of ether and 1.4 ml. of water. The U.V. of the ether layer ($\lambda_{max}$ 318) shows a 50% recovery, and that of the water layer ($\lambda_{max}$ 285) 10% of starting absorbance. Electrophoresis of a 5 μl. sample of the aqueous layer at pH 7, 50 V/cm for 20 minutes followed by bioautography on plates seeded with *S. aureus* shows two zones of inhibition: +0.5 cm (19 mm diameter) and +4 cm (25 mmoles). The slower moving spot is O- methyl Thienamycin; the faster moving spot is O-methyl-N-carbobenzyloxy Thienamycin. Substantially pure O-Methyl Thienamycin is obtained from the aqueous phase by chromatography or XAD-2 resin using 10% aqueous THF as eluting solvent.

EXAMPLE 28

Preparation of O-Acetyl-Thienamycin

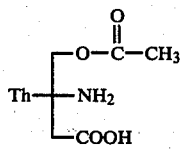

Step A: O-Acetyl-N-(p-Nitrobenzyloxycarbonyl)-Thienamycin-(p-Nitrobenzyl)-Ester To a solution of 50 mg. of N-(p-nitrobenzyloxy-carbonyl)-Thienamycin-(p-nitrobenzyl)ester in 0.5 ml. pyridine is added 0.16 ml. of acetic anhydride. The mixture is allowed to react at 25° C. for 3 hours, then pumped to dryness under vacuum. The solid residue is dissolved in chloroform and chromatographed on an 8"×8" silica gel plate in 3:1 ethylacetate-chloroform. The band at $R_f$ 0.55 is isolated yielding 36 mg. of O-acetyl N-(p-nitro-benzyl-oxycarbonyl)-Thienamycin-(p-nitrobenzyl ester; m.p. 172°–175° C. NMR (CDCl$_3$)$\tau$, 1.41, (d J=6 HZ C$\underline{H}_3$); 2.04 (s, COCH$_3$), 2.7–3.6 (m); 4.14 (t of d) (J=3 and 9 Hz); 5.17 (s, carbamyl C$\underline{H}_2$); 5.35 (AB quartet, J=14 Hz), 7.45 (d), 7.60 (d), 8.18 (d) (J=9 Hz, aromatic H) Ms. M+ m/e 628.

Step B: O-Acetyl-Thienamycin

A solution of O-acetyl-N-(p-nitrobenzyloxycarbonyl) Thienamycin- (p-nitrobenzyl) ester (20 mg.) in tetrahydrofuran ethanol (2.5:1) is hydrogenated at 40 psig. at 23° C. In the presence of 20 mg. of platinum oxide for 1 hour. The catalyst is filtered and the filtrate is diluted with 1 ml. of 0.1 N pH 7 phosphate buffer and evaporated to the cloud point. The mixture is taken up in 5 ml. of ethylacetate and 5 ml. of water and separated. The ethylacetate layer is extracted with pH 3 phosphate buffer. The combined aqueous extracts are adjusted to pH 7 and extracted with ethylacetate and with ether. The aqueous phase is concentrated and chromatographed on 4 ml. of XAD-2 resin. The column is first eluted with 40 ml. of water and then the product is eluted with 10% tetrahydrofuran. High pressure liquid chromatography on C$_{18}$ Porosil with 10% THF gives one peak with a retention time of 8 minutes vs. 5 minutes for Thienamycin. The THF elute is evaporated to a small volume (u.v. $\lambda_{max}$ 297 m$\mu$), and freeze dried to give O-acetyl-Thienamycin as a white powder.

EXAMPLE 29

Preparation of Thienamycin O-Methanesulfonyl

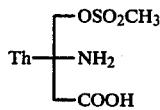

Step A: N-(p-nitrobenzyloxycarbonyl)Thienamycin O-methanesulfonyl p-nitrobenzyl ester

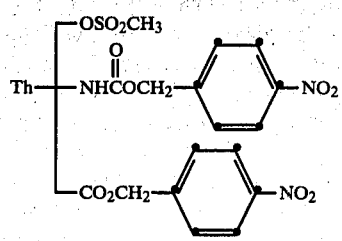

Methanesulfonyl chloride (34 mg.) in CH$_2$Cl$_2$ (0.8 ml.) is added dropwise over 5 minutes to an ice-cold, stirred solution of N-(p-nitrobenzyloxycarbonyl)-Thienamycin-p-nitrobenzyl ester (117 mg.) and triethylamine (40 mg.) in anhydrous CH$_2$Cl$_2$ (6 ml.). After stirring for 1.5 hours more, the reaction mixture is diluted with cold CH$_2$Cl$_2$ (20 ml.), washed with water (3° C., 10 ml.), 0.1 M pH 3 phosphate buffer (3° C., 5 ml.), and 2% aqueous NaHCO$_3$ (3° C.), dried with MgSO$_4$ and filtered. Evaporation of the solvent in vacuo leaves p-nitrobenzyl-6(1-methanesulfonyloxyethyl)-3-[2-(p-nitrobenzyloxycarbonylamino)ethylthio]-7-oxo-1-azabicyclo[3.2.0]-hept-2-ene-2-carboxylate (otherwise referred to as N-(p-nitrobenzyloxy-carbonyl)Thienamycin O-methanesulfonyl p-nitrobenzyl ester, for convenience) as oil.

Step B: Thienamycin O-Methanesulfonyl

Following the hydrogenation procedure of Example 4, Step B, the title compound is obtained when the indicated substitution is made in equivalent amounts.

EXAMPLE 30

O-Sulfo-Thienamycin

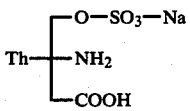

To a solution of 50 mg of N-(p-nitrobenzyloxycarbonyl) Thienamycin (p-nitrobenzyl) ester in 0.5 ml of pyridine is added 20 mg. of pyridine sulfuric anhydride. The mixture is allowed to react at 25° for 4 hours then the excess pyridine is removed under reduced pressure. The residue is stirred with 20 ml. each of methylene chloride and 0.1% sodium bicarbonate solution for 30 minutes then the aqueous layer is separated and freeze dried. The solid residue containing O-sulfo-N-(p-nitrobenzyloxycarbonyl)- Thienamycin-(p-nitrobenzyl)ester, sodium salt is dissolved in 20 ml. of 1:1 aqueous dioxane and hydrogenated for four hours in the presence of 5.0 mg. of platinum oxide catalyst at 40 PSIG. The catalyst is filtered and the filtrate is extracted twice with ethylacetate. The aqueous layer is concentrated to 5 ml. and chromatographed on 40 ml. of XAD-2 resin. The column is eluted with water and the fraction containing o-sulfo Thienamycin sodium slat is recovered and freeze dried.

EXAMPLE 31

Preparation of Pharmaceutical Compositions

One such unit dosage form consists in mixing 120 mg. of Thienamycin O-phosphate ester disodium salt with 20 mg. of lactose and 5 mg. of magnesium stearate and placing the 145 mg. mixture into a No. 3 gelatin capsule. Similarly, by employing more of the active ingredient and less lactose, other dosage forms can be put up in No. 3 gelatin capsules and should it be necessary to mix more than 145 mg. of ingredients together, larger capsules such as compressed tablets and pills can also be prepared. The following examples are illustrative of the preparation of pharmaceutical formulations:

| TABLET | PER TABLET |
|---|---|
| Thienamycin O-phosphate Ester Disodium Salt | 125 mg. |
| Cornstarch, U.S.P. | 6 mg. |
| Dicalcium Phosphate | 192 mg. |
| Lactose, U.S.P. | 190 mg. |

The active ingredient is blended with the dicalcium phosphate, lactose and about half of the cornstarch. The mixture is then granulated with a 15% cornstarch paste (6 mg.) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| | PER TABLET |
|---|---|
| PARENTERAL SOLUTION | |
| Ampoule: | |
| Thienamycin O-phosphate Ester Disodium Salt | 500 mg. |
| Diluent: Sterile Water for Injection | 2 cc. |
| OPTHALMIC SOLUTION | |
| Thienamycin O-phosphate Ester Disodium Salt | 100 mg. |
| Hydroxypropylmethyl Cellulose | 5 mg. |
| Sterile Water to | 1 ml. |
| OTIC SOLUTION | |
| Thienamycin O-phosphate Ester Disodium Salt | 100 mg. |
| Benzalkonium Chloride | 0.1 mg. |
| Sterile Water to | 1 ml. |
| TOPICAL OINTMENT | |
| Thienamycin O-phosphate Ester Disodium Salt | 100 mg. |
| Polyethylene Glycol 4000 U.S.P. | 400 mg. |
| Polyethylene Glycol 400 U.S.P. | 1.0 gram |

The active ingredient in the above formulations may be administered alone or in combination with other biologically active ingredients as, for example, with other antibacterial agents such as lincomycin, a penicillin. streptomycin, novobiocin, gentamicin, neomycin, colistin and kanamycin, or with other therapeutic agents such as probenecid.

What is claimed is:

1. The compound having the structural formula:

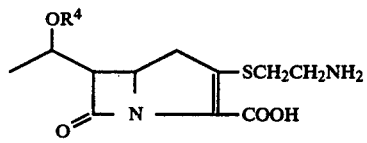

and the non-toxic, pharmaceutically acceptable salts thereof; wherein $R^4$ is lower alkyl, phosphono, lower alkylcarbamoyl, lower alkoxylower alkyl, lower alkanoyl, methanesulfono, or sulfo, the designation lower alkyl, lower alkanoyl, or lower alkoxy having 1–6 carbon atoms.

2. The compound of claim 1 wherein $R^4$ is methyl, acetyl, methoxymethyl, sulfo, phosphono, methylcarbamoyl, or methanesulfono.

* * * * *